United States Patent
Jungkamp et al.

(10) Patent No.: US 7,504,529 B2
(45) Date of Patent: Mar. 17, 2009

(54) METHOD FOR HYDROCYANATION

(75) Inventors: Tim Jungkamp, Kapellen (BE); Hans-Martin Polka, Mannheim (DE); Robert Baumann, Mannheim (DE); Michael Bartsch, Neustadt (DE); Gerd Haderlein, Grünstadt (DE); Hermann Luyken, Ludwigshafen (DE); Jens Scheidel, Hirschberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 463 days.

(21) Appl. No.: 10/587,027

(22) PCT Filed: Jan. 26, 2005

(86) PCT No.: PCT/EP2005/000724

§ 371 (c)(1), (2), (4) Date: Jul. 24, 2006

(87) PCT Pub. No.: WO2005/073178

PCT Pub. Date: Aug. 11, 2005

(65) Prior Publication Data

US 2008/0242885 A1    Oct. 2, 2008

(30) Foreign Application Priority Data

Jan. 29, 2004    (DE) .................. 10 2004 004 718

(51) Int. Cl.
*C07C 253/08*    (2006.01)
(52) U.S. Cl. .................................... 558/332
(58) Field of Classification Search ............... None
See application file for complete search history.

(56) References Cited

U.S. PATENT DOCUMENTS

| 3,947,487 | A | 3/1976 | Crooks |
|---|---|---|---|
| 6,020,516 | A | 2/2000 | Foo et al. |
| 6,169,198 | B1 | 1/2001 | Fischer et al. |
| 6,197,992 | B1 | 3/2001 | Fischer et al. |
| 6,242,633 | B1 | 6/2001 | Fischer et al. |
| 6,355,833 | B2 | 3/2002 | Fischer et al. |
| 6,521,778 | B1 | 2/2003 | Fischer et al. |
| 6,770,770 | B1 | 8/2004 | Baumann et al. |
| 2003/0100442 | A1 | 5/2003 | Chu et al. |

FOREIGN PATENT DOCUMENTS

| DE | 24 50 863 | 5/1975 |
|---|---|---|
| DE | 19953058 A1 | 5/2001 |
| DE | 100 46 025 A1 | 3/2002 |
| DE | 100 38 037 A1 | 4/2002 |
| DE | 100 50 286 A1 | 4/2002 |
| DE | 101 50 285 A1 | 4/2003 |
| DE | 10207165 | 8/2003 |
| DE | 103 50 999 A1 | 6/2005 |
| DE | 10 2004 004 684 A1 | 8/2005 |
| DE | 10 2004 004 724 A1 | 8/2005 |
| EP | 1 218 389 B1 | 10/2003 |
| WO | WO-98/27054 | 6/1998 |
| WO | WO-99/13983 | 3/1999 |
| WO | WO-99/64155 | 12/1999 |
| WO | WO-01/04392 A1 | 1/2001 |

OTHER PUBLICATIONS

Kirk-Othmer, Encyclopedia of Chemical Technology, 4. Ed., vol. 20; John-Wiley & Sons, New York; 1996; p. 1040-1055.
Kirk-Othmer, Encyclopedia of Chemical Technology, 4. Ed., vol. 8: John-Wiley & Sons, New York; 1996; p. 334-348.

*Primary Examiner*—Kamal A Saeed
(74) *Attorney, Agent, or Firm*—Connolly Bove Lodge & Hutz LLP

(57) ABSTRACT

A process is described for removing hydrogen cyanide from mixtures comprising pentenenitrile, wherein the removal is effected by an azeotropic distillation of hydrogen cyanide with 1,3-butadiene.

11 Claims, No Drawings

METHOD FOR HYDROCYANATION

CROSS REFERENCE TO RELATED APPLICATIONS

This application is a National Phase of PCT/EP2005/000724, filed on Jan. 26, 2005, which claims priority to German application no. 102004004718.9, filed Jan. 29, 2004.

The present invention relates to a process for removing hydrogen cyanide from mixtures comprising pentenenitrile and hydrogen cyanide.

Adiponitrile, an important intermediate in nylon production, is prepared by double hydrocyanation of 1,3-butadiene. In a first hydrocyanation, 1,3-butadiene is reacted with hydrogen cyanide in the presence of nickel(0) which is stabilized with phosphorus ligands to give 3-pentenenitrile. Secondary components of this first hydrocyanation are substantially 2-methyl-3-butenenitrile, 2-pentenenitriles, 2-methyl-2-butenenitriles, $C_9$ nitriles, methylglutaronitrile and 4-vinylcyclohexene. In a second hydrocyanation, 3-pentenenitrile is subsequently reacted with hydrogen cyanide to give adiponitrile, likewise over a nickel catalyst, but with addition of a Lewis acid.

In the first hydrocyanation, 1,3-butadiene is used in a stoichiometric excess in relation to hydrogen cyanide in the hydrocyanation reaction. In the hydrocyanation reaction, the hydrogen cyanide used reacts virtually fully. However, a residual content of hydrogen cyanide of up to 5000 ppm by weight remains in the reaction effluent from this hydrocyanation. This residual content of hydrogen cyanide leads, in the downstream process stages in which the hydrocyanation catalyst is removed from the reaction product of the pentenenitrile isomers, as a result of heating, to fouling and formation of solids which comprise nickel(II) cyanide.

In the hydrocyanation effluents, hydrogen cyanide is present not only as a physically dissolved component, but also as a species chemically bound to the nickel complex. Owing to this, the vapor pressure observed of the hydrogen cyanide in the reaction mixture is frequently lower than that calculated by Raoult's law from the mole fraction and the vapor pressure of the hydrogen cyanide. This vapor pressure reduction complicates the removal of hydrogen cyanide from mixtures comprising pentenenitrile by distillation.

In order to fully remove residues of hydrogen cyanide from hydrocyanation effluents by distillation in industrial practice, the following routes are generally proposed, a full removal of hydrogen cyanide meaning that the hydrocyanation effluent, after removal of the hydrogen cyanide, still has a residual content of from 0 to 500 ppm of hydrogen cyanide. For instance, either very low pressures and moderate temperatures of from 50 to 70° C. in the bottom of a suitable distillation apparatus are used in order to fully remove hydrogen cyanide by distillation. However, product of value in the form of isomers of pentenenitrile also distills over in some circumstances. Lower pressures additionally entail low condensation temperatures for the material distilled off which has to be recycled into the process for economic reasons. The employment of high temperatures, for example from 70 to 120° C., is industrially realizable, but simultaneously leads to residues of hydrogen cyanide reacting with the nickel catalyst to give solids which comprise nickel(II) cyanide, and thus results in fouling in the evaporator stages.

It is accordingly an object of the present invention to provide a process for reducing the content of hydrogen cyanide in mixtures comprising pentenenitrile and hydrogen cyanide which avoids the above-described disadvantages.

The achievement of this object is based on a process for reducing the content of hydrogen cyanide in mixtures comprising pentenenitriles. In the process according to the invention, the reduction of the content of hydrogen cyanide is effected by a removal of hydrogen cyanide by means of an azeotropic distillation with 1,3-butadiene.

The inventive principle is based on the effect that hydrogen cyanide always gets into the vapor phase when 1,3-butadiene is evaporated from a reaction effluent of hydrocyanations. It has been found in accordance with the invention that even in a fractional distillation of 1,3-butadiene from mixtures which comprise 1,3-butadiene (b.p.$^{1013\ mbar}$=−4° C.) and hydrogen cyanide (b.p.$^{1013\ mbar}$=+27° C.), despite the great boiling point difference of 31° C., hydrogen cyanide is always present in the top effluent. Hydrogen cyanide and 1,3-butadiene form a boiling point minimum azeotrope, so that, irrespective of the conditions under which the hydrocyanation effluent is partly evaporated, hydrogen cyanide always distills over in mixtures with 1,3-butadiene.

In a particularly preferred embodiment, the process according to the invention is characterized by the following process steps:

(1) hydrocyanating 1,3-butadiene by its reaction with hydrogen cyanide in the presence of at least one hydrocyanation catalyst to obtain a hydrocyanation stream which comprises 3-pentenenitrile, 2-methyl-3-butenenitrile, hydrogen cyanide, 1,3-butadiene and the at least one hydrocyanation catalyst, (2) removing a mixture of hydrogen cyanide and 1,3-butadiene which forms an azeotrope from the hydrocyanation stream by distillation.

The hydrocyanation of 1,3-butadiene to 3-pentenenitrile is carried out in the presence of a nickel(0) catalyst complex.

The Ni(0) complexes which contain phosphorus ligands and/or free phosphorus ligands are preferably homogeneously dissolved nickel(0) complexes.

The phosphorus ligands of the nickel(0) complexes and the free phosphorus ligands are preferably selected from mono- or bidentate phosphines, phosphites, phosphinites and phosphonites.

These phosphorus ligands preferably have the formula I:

$$P(X^1R^1)(X^2R^2)(X^3R^3) \qquad (I)$$

In the context of the present invention, compound I is a single compound or a mixture of different compounds of the aforementioned formula.

According to the invention, $X^1$, $X^2$, $X^3$ each independently are oxygen or a single bond. When all of the $X^1$, $X^2$ and $X^3$ groups are single bonds, compound I is a phosphine of the formula $P(R^1, R^2, R^3)$ with the definitions of $R^1$, $R^2$ and $R^3$ specified in this description.

When two of the $X^1$, $X^2$ and $X^3$ groups are single bonds and one is oxygen, compound I is a phosphinite of the formula $P(OR^1)(R^2)(R^3)$ or $P(R^1)(OR^2)(R^3)$ or $P(R^1)(R^2)(OR^3)$ with the definitions of $R^1$, $R^2$ and $R^3$ specified hereinbelow.

When one of the $X^1$, $X^2$ and $X^3$ groups is a single bond and two are oxygen, compound I is a phosphonite of the formula $P(OR^1)(OR^2)(R^3)$ or $P(R^1)(OR^2)(OR^3)$ or $P(OR^1)(R^2)(OR^3)$ with the definitions of $R^1$, $R^2$ and $R^3$ specified in this description.

In a preferred embodiment, all $X^1$, $X^2$ and $X^3$ groups should be oxygen, so that compound I is advantageously a phosphite of the formula $P(OR^1)(OR^2)(OR^3)$ with the definitions of $R^1$, $R^2$ and $R^3$ specified hereinbelow.

According to the invention, $R^1$, $R^2$, $R^3$ are each independently identical or different organic radicals. $R^1$, $R^2$ and $R^3$ are each independently alkyl radicals preferably having from 1 to 10 carbon atoms, such as methyl, ethyl, n-propyl, i-propyl, n-butyl, i-butyl, s-butyl, t-butyl, aryl groups such as phenyl, o-tolyl, m-tolyl, p-tolyl, 1-naphthyl, 2-naphthyl, or hydrocarbyl, preferably having from 1 to 20 carbon atoms, such as 1,1'-biphenol, 1,1'-binaphthol. The $R^1$, $R^2$ and $R^3$ groups may be bonded together directly, i.e. not solely via the central phosphorus atom. Preference is given to the $R^1$, $R^2$ and $R^3$ groups not being bonded together directly.

In a preferred embodiment, $R^1$, $R^2$ and $R^3$ are radicals selected from the group consisting of phenyl, o-tolyl, m-tolyl and p-tolyl. In a particularly preferred embodiment, a maximum of two of the $R^1$, $R^2$ and $R^3$ groups should be phenyl groups.

In another preferred embodiment, a maximum of two of the $R^1$, $R^2$ and $R^3$ groups should be o-tolyl groups.

Particularly preferred compounds I which may be used are those of the formula I a

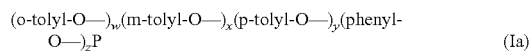

(Ia)

where w, x, y and z are each a natural number and the following conditions apply: w+x+y+z=3 and w, z≦2.

Such compounds I a are, for example, (p-tolyl-O—)(phenyl-O—)$_2$P, (m-tolyl-O—)(phenyl-O—)$_2$P, (o-tolyl-O—)(phenyl-O—)$_2$P, (p-tolyl-O—)$_2$(phenyl-O—)P, (m-tolyl-O—)$_2$(phenyl-O—)P, (o-tolyl-O—)$_2$(phenyl-O—)P, (m-tolyl-O—)(p-tolyl-O—)(phenyl-O—)P, (o-tolyl-O—)(p-tolyl-O)(phenyl-O—)P, (o-tolyl-O—)(m-tolyl-O—)(phenyl-O—)P, (p-tolyl-O—)$_3$P, (m-tolyl-O—)(p-tolyl-O—)$_2$P, (o-tolyl-O—)(p-tolyl-O—)$_2$P, (m-tolyl-O—)$_2$(p-tolyl-O—)P, (o-tolyl-O—)$_2$(p-tolyl-O—)P, (o-tolyl-O—)(m-tolyl-O—)(p-tolyl-O—)P, (m-tolyl-O—)$_3$P, (o-tolyl-O—)(m-tolyl-O—)$_2$P (o-tolyl-O—)$_2$(m-tolyl-O—)P or mixtures of such compounds.

For example, mixtures comprising (m-tolyl-O—)$_3$P, (m-tolyl-O—)$_2$(p-tolyl-O—)P, (m-tolyl-O—)(p-tolyl-O—)$_2$P and (p-tolyl-O—)$_3$P may be obtained by reacting a mixture comprising m-cresol and p-cresol, in particular in a molar ratio of 2:1, as obtained in the distillative workup of crude oil, with a phosphorus trihalide, such as phosphorus trichloride.

In another, likewise preferred embodiment, the phosphorus ligands are the phosphites, described in detail in DE-A 199 53 058, of the formula I b:

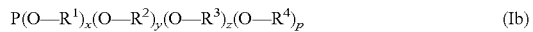

(Ib)

where $R^1$: aromatic radical having a $C_1$-$C_{18}$-alkyl substituent in the o-position to the oxygen atom which joins the phosphorus atom to the aromatic system, or having an aromatic substituent in the o-position to the oxygen atom which joins the phosphorus atom to the aromatic system, or having a fused aromatic system in the o-position to the oxygen atom which joins the phosphorus atom to the aromatic system, $R^2$: aromatic radical having a $C_1$-$C_{18}$-alkyl substituent in the m-position to the oxygen atom which joins the phosphorus atom to the aromatic system, or having an aromatic substituent in the m-position to the oxygen atom which joins the phosphorus atom to the aromatic system, or having a fused aromatic system in the m-position to the oxygen atom which joins the phosphorus atom to the aromatic system, the aromatic radical bearing a hydrogen atom in the o-position to the oxygen atom which joins the phosphorus atom to the aromatic system, $R^3$: aromatic radical having a $C_1$-$C_{18}$-alkyl substituent in the p-position to the oxygen atom which joins the phosphorus atom to the aromatic system, or having an aromatic substituent in the p-position to the oxygen atom which joins the phosphorus atom to the aromatic system, the aromatic radical bearing a hydrogen atom in the o-position to the oxygen atom which joins the phosphorus atom to the aromatic system, $R^4$: aromatic radical which bears substituents other than those defined for $R^1$, $R^2$ and $R^3$ in the o-, m- and p-position to the oxygen atom which joins the phosphorus atom to the aromatic system, the aromatic radical bearing a hydrogen atom in the o-position to the oxygen atom which joins the phosphorus atom to the aromatic system, x: 1 or 2, y, z, p: each independently 0, 1 or 2, with the proviso that x+y+z+p=3.

Preferred phosphites of the formula I b can be taken from DE-A 199 53 058. The $R^1$ radical may advantageously be o-tolyl, o-ethylphenyl, o-n-propylphenyl, o-isopropyl-phenyl, o-n-butylphenyl, o-sec-butylphenyl, o-tert-butylphenyl, (o-phenyl)phenyl or 1-naphthyl groups.

Preferred $R^2$ radicals are m-tolyl, m-ethylphenyl, m-n-propylphenyl, m-isopropylphenyl, m-n-butylphenyl, m-sec-butylphenyl, m-tert-butylphenyl, (m-phenyl)phenyl or 2-naphthyl groups.

Advantageous $R^3$ radicals are p-tolyl, p-ethylphenyl, p-n-propylphenyl, p-isopropyl-phenyl, p-n-butylphenyl, p-sec-butylphenyl, p-tert-butylphenyl or (p-phenyl)phenyl groups.

The $R^4$ radical is preferably phenyl. p is preferably zero. For the indices x, y, z and p in compound I b, there are the following possibilities:

| x | y | z | p |
|---|---|---|---|
| 1 | 0 | 0 | 2 |
| 1 | 0 | 1 | 1 |
| 1 | 1 | 0 | 1 |
| 2 | 0 | 0 | 1 |
| 1 | 0 | 2 | 0 |
| 1 | 1 | 1 | 0 |
| 1 | 2 | 0 | 0 |
| 2 | 0 | 1 | 0 |
| 2 | 1 | 0 | 0 |

Preferred phosphites of the formula I b are those in which p is zero, and $R^1$, $R^2$ and $R^3$ are each independently selected from o-isopropylphenyl, m-tolyl and p-tolyl, and $R^4$ is phenyl.

Particularly preferred phosphites of the formula I b are those in which $R^1$ is the o-isopropylphenyl radical, $R^2$ is the m-tolyl radical and $R^3$ is the p-tolyl radical with the indices specified in the table above; also those in which $R^1$ is the o-tolyl radical, $R^2$ is the m-tolyl radical and $R^3$ is the p-tolyl radical with the indices specified in the table; additionally those in which $R^1$ is the 1-naphthyl radical, $R^2$ is the m-tolyl radical and $R^3$ is the p-tolyl radical with the indices specified in the table; also those in which $R^1$ is the o-tolyl radical, $R^2$ is the 2-naphthyl radical and $R^3$ is the p-tolyl radical with the indices specified in the table; and finally those in which $R^1$ is the o-isopropylphenyl radical, $R^2$ is the 2-naphthyl radical and $R^3$ is the p-tolyl radical with the indices specified in the table; and also mixtures of these phosphites.

Phosphites of the formula I b may be obtained by a) reacting a phosphorus trihalide with an alcohol selected from the group consisting of $R^1OH$, $R^2OH$, $R^3OH$ and $R^4OH$ or mixtures thereof to obtain a dihalophosphorous monoester, b) reacting the dihalophosphorous monoester mentioned with an alcohol selected from the group consisting of $R^1OH$, $R^2OH$, $R^3OH$ and $R^4OH$ or mixtures thereof to obtain a monohalophosphorous diester and c) reacting the monohalophosphorous diester mentioned with an alcohol selected from the group consisting of $R^1OH$, $R^2OH$, $R^3OH$ and $R^4OH$ or mixtures thereof to obtain a phosphite of the formula I b.

The reaction may be carried out in three separate steps. Equally, two of the three steps may be combined, i.e. a) with b) or b) with c). Alternatively, all of the steps a), b) and c) may be combined together.

Suitable parameters and amounts of the alcohols selected from the group consisting of $R^1OH$, $R^2OH$, $R^3OH$ and $R^4OH$ or mixtures thereof may be determined readily by a few simple preliminary experiments.

Useful phosphorus trihalides are in principle all phosphorus trihalides, preferably those in which the halide used is Cl, Br, I, in particular Cl, and mixtures thereof. It is also possible to use mixtures of various identically or differently halogen-substituted phosphines as the phosphorus trihalide. Particular preference is given to $PCl_3$. Further details on the reaction conditions in the preparation of the phosphites I b and for the workup can be taken from DE-A 199 53 058.

The phosphites I b may also be used in the form of a mixture of different phosphites I b as a ligand. Such a mixture may be obtained, for example, in the preparation of the phosphites I b.

However, preference is given to the phosphorus ligand being multidentate, in particular bidentate. The ligand used therefore preferably has the formula II

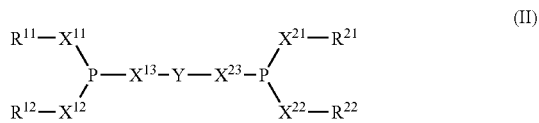

(II)

where $X^{11}$, $X^{12}$, $X^{13}$, $X^{21}$, $X^{22}$, $X^{23}$ are each independently oxygen or a single bond $R^{11}$, $R^{12}$ are each independently identical or different, separate or bridged organic radicals $R^{21}$, $R^{22}$ are each independently identical or different, separate or bridged organic radicals, Y is a bridging group.

In the context of the present invention, compound II is a single compound or a mixture of different compounds of the aforementioned formula.

In a preferred embodiment, $X^{11}$, $X^{12}$, $X^{13}$, $X^{21}$, $X^{22}$, $X^{23}$ may each be oxygen. In such a case, the bridging group Y is bonded to phosphite groups.

In another preferred embodiment, $X^{11}$ and $X^{12}$ may each be oxygen and $X^{13}$ a single bond, or $X^{11}$ and $X^{13}$ each oxygen and $X^{12}$ a single bond, so that the phosphorus atom surrounded by $X^{11}$, $X^{12}$ and $X^{13}$ is the central atom of a phosphonite. In such a case, $X^{21}$, $X^{22}$ and $X^{23}$ may each be oxygen, or $X^{21}$ and $X^{22}$ may each be oxygen and $X^{23}$ a single bond, or $X^{21}$ and $X^{23}$ may each be oxygen and $X^{22}$ a single bond, or $X^{23}$ may be oxygen and $X^{21}$ and $X^{22}$ each a single bond, or $X^{21}$ may be oxygen and $X^{22}$ and $X^{23}$ each a single bond, or $X^{21}$, $X^{22}$ and $X^{23}$ may each be a single bond, so that the phosphorus atom surrounded by $X^{21}$, $X^{22}$ and $X^{23}$ may be the central atom of a phosphite, phosphonite, phosphinite or phosphine, preferably a phosphonite.

In another preferred embodiment, $X^{13}$ may be oxygen and $X^{11}$ and $X^{12}$ each a single bond, or $X^{11}$ may be oxygen and $X^{12}$ and $X^{13}$ each a single bond, so that the phosphorus atom surrounded by $X^{11}$, $X^{12}$ and $X^{13}$ is the central atom of a phosphonite. In such a case, $X^{21}$, $X^{22}$ and $X^{23}$ may each be oxygen, or $X^{23}$ may be oxygen and $X^{21}$ and $X^{22}$ each a single bond, or $X^{21}$ may be oxygen and $X^{22}$ and $X^{23}$ each a single bond, or $X^{21}$, $X^{22}$ and $X^{23}$ may each be a single bond, so that the phosphorus atom surrounded by $X^{21}$, $X^{22}$ and $X^{23}$ may be the central atom of a phosphite, phosphinite or phosphine, preferably a phosphinite.

In another preferred embodiment, $X^{11}$, $X^{12}$ and $X^{13}$ may each be a single bond, so that the phosphorus atom surrounded by $X^{11}$, $X^{12}$ and $X^{13}$ is the central atom of a phosphine. In such a case, $X^{21}$, $X^{22}$ and $X^{23}$ may each be oxygen, or $X^{21}$, $X^{22}$ and $X^{23}$ may each be a single bond, so that the phosphorus atom surrounded by $X^{21}$, $X^{22}$ and $X^{23}$ may be the central atom of a phosphite or phosphine, preferably a phosphine.

The bridging group Y is advantageously an aryl group which is substituted, for example by $C_1$-$C_4$-alkyl, halogen, such as fluorine, chlorine, bromine, halogenated alkyl, such as trifluoromethyl, aryl, such as phenyl, or is unsubstituted, preferably a group having from 6 to 20 carbon atoms in the aromatic system, in particular pyrocatechol, bis(phenol) or bis(naphthol).

The $R^{11}$ and $R^{12}$ radicals may each independently be identical or different organic radicals. Advantageous $R^{11}$ and $R^{12}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{21}$ and $R^{22}$ radicals may each independently be identical or different organic radicals. Advantageous $R^{21}$ and $R^{22}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{11}$ and $R^{12}$ radicals may each be separate or bridged. The $R^{21}$ and $R^{22}$ radicals may also each be separate or bridged. The $R^{11}$, $R^{12}$, $R^{21}$ and $R^{22}$ radicals may each be separate, two may be bridged and two separate, or all four may be bridged, in the manner described.

In a particularly preferred embodiment, useful compounds are those of the formula I, II, III, IV and V specified in U.S. Pat. No. 5,723,641. In a particularly preferred embodiment, useful compounds are those of the formula I, II, III, IV, V, VI and VII specified in U.S. Pat. No. 5,512,696, in particular the compounds used there in examples 1 to 31. In a particularly preferred embodiment, useful compounds are those of the formula I, II, III, IV, V, VI, VII, VIII, IX, X, XI, XII, XIII, XIV and XV specified in U.S. Pat. No. 5,821,378, in particular the compounds used there in examples 1 to 73.

In a particularly preferred embodiment, useful compounds are those of the formula I, II, III, IV, V and VI specified in U.S. Pat. No. 5,512,695, in particular the compounds used there in examples 1 to 6. In a particularly preferred embodiment, useful compounds are those of the formula I, II, III, IV, V, VI, VII, VIII, IX, X, XI, XII, XIII and XIV specified in U.S. Pat. No. 5,981,772, in particular the compounds used there in examples 1 to 66.

In a particularly preferred embodiment, useful compounds are those specified in U.S. Pat. No. 6,127,567 and the compounds used there in examples 1 to 29. In a particularly preferred embodiment, useful compounds are those of the formula I, II, III, IV, V, VI, VII, VIII, IX and X specified in U.S. Pat. No. 6,020,516, in particular the compounds used there in examples 1 to 33. In a particularly preferred embodiment, useful compounds are those specified in U.S. Pat. No. 5,959,135, and the compounds used there in examples 1 to 13.

In a particularly preferred embodiment, useful compounds are those of the formula I, II and III specified in U.S. Pat. No. 5,847,191. In a particularly preferred embodiment, useful compounds are those specified in U.S. Pat. No. 5,523,453, in particular the compounds illustrated there in formula 1, 2, 3, 4, 5, 6, 7, 8, 9, 10, 11, 12, 13, 14, 15, 16, 17, 18, 19, 20 and 21. In a particularly preferred embodiment, useful compounds are those specified in WO 01/14392, preferably the compounds illustrated there in formula V, VI, VII, VIII, IX, X, XI, XII, XIII, XIV, XV, XVI, XVII, XXI, XXII, XXIII.

In a particularly preferred embodiment, useful compounds are those specified in WO 98/27054. In a particularly preferred embodiment, useful compounds are those specified in WO 99/13983. In a particularly preferred embodiment, useful compounds are those specified in WO 99/64155.

In a particularly preferred embodiment, useful compounds are those specified in the German patent application DE 100 380 37. In a particularly preferred embodiment, useful compounds are those specified in the German patent application DE 100 460 25. In a particularly preferred embodiment, useful compounds are those specified in the German patent application DE 101 502 85.

In a particularly preferred embodiment, useful compounds are those specified in the German patent application DE 101 502 86. In a particularly preferred embodiment, useful compounds are those specified in the German patent application DE 102 071 65. In a further particularly preferred embodiment of the present invention, useful phosphorus chelate ligands are those specified in US 2003/0100442 A1.

In a further particularly preferred embodiment of the present invention, useful phosphorus chelate ligands are those specified in the German patent application reference no. DE 103 50 999.2 of Oct. 30, 2003, which has an earlier priority date but was unpublished at the priority date of the present application.

The compounds I, I a, I b and II described and their preparation are known per se. Phosphorus ligands used may also be mixtures comprising at least two of the compounds I, I a, I b and II.

In a particularly preferred embodiment of the process according to the invention; the phosphorus ligand of the nickel(0) complex and/or the free phosphorus ligand is selected from tritolyl phosphite, bidentate phosphorus chelate ligands and the phosphites of the formula I b

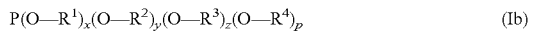  (Ib)

where $R^1$, $R^2$ and $R^3$ are each independently selected from o-isopropylphenyl, m-tolyl and p-tolyl, $R^4$ is phenyl; x is 1 or 2, and y, z, p are each independently 0, 1 or 2 with the proviso that $x+y+z+p=3$; and mixtures thereof.

The hydrocyanation may be carried out in any suitable apparatus known to those skilled in the art. Useful apparatus for the reaction is that which is customary, as described, for example, in: Kirk-Othmer, Encyclopedia of Chemical Technology, 4th Ed. Vol. 20, John Wiley & Sons, New York 1996, pages 1040 to 1055, such as stirred tank reactors, loop reactors, gas circulation reactors, bubble column reactors or tubular reactors, in each case if appropriate with apparatus to remove heat of reaction. The reaction may be carried out in a plurality of, such as two or three, apparatuses.

In a preferred embodiment of the process according to the invention, reactors having backmixing characteristics or batteries of reactors having backmixing characteristics have been found to be advantageous. It has been found that batteries of reactors having backmixing characteristics and which are operated in crossflow mode in relation to the metering of hydrogen cyanide are particularly advantageous.

The hydrocyanation may be carried out in batch mode, continuously or in semibatchwise operation.

Preference is given to carrying out the hydrocyanation continuously in one or more stirred process steps. When a plurality of process steps is used, it is preferred that the process steps are connected in series. In this case, the product from one process step is transferred directly into the next process step. The hydrogen cyanide may be added directly into the first process step or between the individual process steps.

When the hydrocyanation is carried out in semibatchwise operation, it is preferred that the reactor is initially charged with the catalyst components and 1,3-butadiene, while hydrogen cyanide is metered into the reaction mixture over the reaction time.

The hydrocyanation may be carried out in the presence or in the absence of a solvent. When a solvent is used, the solvent should be liquid and inert toward the unsaturated compounds and the at least one catalyst at the given reaction temperature and the given reaction pressure. In general, the solvents used are hydrocarbons, for example benzene or xylene, or nitriles, for example acetonitrile or benzonitrile. However, preference is given to using a ligand as the solvent.

The hydrocyanation may be carried out by charging the apparatus with all reactants. However, it is preferred when the apparatus is filled with the at least one catalyst, 1,3-butadiene and, if appropriate, the solvent. The gaseous hydrogen cyanide preferably floats over the surface of the reaction mixture or is preferably passed through the reaction mixture. A further procedure for charging the apparatus is the filling of the apparatus with the at least one catalyst, hydrogen cyanide and, if appropriate, the solvent, and slowly feeding the 1,3-butadiene to the reaction mixture. Alternatively, it is also possible that the reactants are introduced into the reactor and the reaction mixture is brought to the reaction temperature at which the hydrogen cyanide is added to the mixture in liquid form. In addition, the hydrogen cyanide may also be added before heating to reaction temperature. The reaction is carried out under conventional hydrocyanation conditions for temperature, atmosphere, reaction time, etc.

The hydrocyanation is carried out preferably at pressures of from 0.1 to 500 MPa, more preferably from 0.5 to 50 MPa, in particular from 1 to 5 MPa. The reaction is carried out preferably at temperatures of from 273 to 473 K, more preferably from 313 to 423 K, in particular at from 333 to 393 K. It has been found that advantageous average mean residence times of the liquid reactor phase are in the range from 0.001 to 100 hours, preferably from 0.05 to 20 hours, more preferably from 0.1 to 5 hours, in each case per reactor.

In one embodiment, the hydrocyanation may be performed in the liquid phase in the presence of a gas phase and, if appropriate, of a solid suspended phase. The starting materials, hydrogen cyanide and 1,3-butadiene, may in each case be metered in liquid or gaseous form.

In a further embodiment, the hydrocyanation may be carried out in the liquid phase, in which case the pressure in the reactor is such that all reactants such as 1,3-butadiene, hydrogen cyanide and the at least one catalyst are metered in liquid form and are present in the liquid phase in the reaction mixture. A solid suspended phase may be present in the reaction mixture and may also be metered together with the at least one catalyst, for example consisting of degradation products of the catalyst system, comprising, inter alia, nickel(II) compounds.

In process step (2), an azeotrope-forming mixture of hydrogen cyanide and 1,3-butadiene from the hydrocyanation stream obtained in process step (1) is removed by distillation.

The 1,3-butadiene used for this purpose in process step (2) preferably stems from process step (1). Alternatively, it is also possible that the 1,3-butadiene used in process step (2) does not stem from the hydrocyanation step (1) and is added to the hydrocyanation stream which leaves process step (1) before the azeotropic distillation. In a further embodiment of the process according to the invention, it is possible that the 1,3-butadiene used in process step (2) stems partly from process step (1) and is also partly added to the hydrocyanation stream which leaves process step (1) before the azeotropic distillation.

A further embodiment provides that all of the 1,3-butadiene which is fed to process step (1) is added to the stream which is conducted from process step (1) to process (2) and then recycled from process step (2) into process step (1).

The 1,3-butadiene fed to process step (2) is preferably depleted in stabilizer and/or water by pretreatment, as described in DE-A-102 004 004 684. In general, the depletion in stabilizer and/or water is effected by contacting the 1,3-butadiene with at least one microporous solid, the microporous solid preferably being started from the group consisting of aluminas and molecular sieves and having a pore size of from 0.01 to 20 mm.

The ratio, based on the mass, of 1,3-butadiene to hydrogen cyanide in process step (2) is preferably from 1 to 2000, more preferably from 2 to 100, in particular from 5 to 40.

The hydrocyanation stream or the mixture comprising pentenenitrile obtained in process step (1) preferably has at least one of the following contents:

from 10 to 99% by weight, more preferably from 15 to 95% by weight, in particular from 20 to 90% by weight, of pentenenitriles comprising trans-3-pentenenitrile, 2-methyl-3-butenenitrile and also further pentenenitrile isomers, the ratio of 2-methyl-3-butenenitrile to trans-3-pentenenitrile being from 0.1:1 to 5:1 depending on the catalyst system and reaction conditions used;

from 0 to 60% by weight, more preferably from 1 to 30% by weight, in particular from 5 to 25% by weight, of 1,3-butadiene;

from 0.01 to 30% by weight, more preferably from 0.01 to 20% by weight, in particular from 0.01 to 10% by weight, of catalyst components including catalyst degradation products;

more preferably from 1 ppm by weight to 5% by weight, in particular from 5 to 5000 ppm by weight, of hydrogen cyanide.

The azeotropic distillation of 1,3-butadiene and hydrogen cyanide in process step (2) is effected preferably at a temperature in the bottom of a suitable distillation apparatus of from 30 to 250° C., more preferably from 40 to 150° C., in particular form 50 to 120° C., and at a temperature in the condensation in a suitable distillation apparatus of from −50 to 150° C., more preferably from −15 to 60° C., in particular from −5 to 45° C. The pressure is preferably from 0.001 to 100 bar, more preferably from 0.01 to 10 bar, in particular from 0.02 to 5 bar.

Process step (2) may be carried out in any suitable apparatus known to those skilled in the art. Suitable apparatus for the distillation is as described, for example, in: Kirk-Othmer, Encyclopedia of Chemical Technology, 4th Ed., Vol. 8, John Wiley & Sons, New York, 1996, pages 334-348, such as sieve tray columns, bubble-cap tray columns, columns having structured packing or random packing, which may also be operated as dividing wall columns. This distillation apparatus is in each case equipped with suitable apparatus for evaporation, such as falling-film evaporators, thin-film evaporators, multiphase helical tube evaporators, natural circulation evaporators or forced circulation flash evaporators, and also with apparatus for condensing the vapor stream.

The distillation may be carried out in a plurality of, such as two or three, apparatuses, preferably in two apparatuses.

A corresponding two-stage distillation as a particularly preferred embodiment is described in DE-A-102 004 004 724, whose disclosure on this subject is incorporated into the present invention by reference.

Accordingly, process step (2) may be carried out in two stages in a process step (2a) and a process step (2b).

Process step (2a) of the process according to the invention may be carried out in any suitable apparatus known to those skilled in the art. Suitable apparatus for the distillation is as described, for example, in: Kirk-Othmer, Encyclopedia of Chemical Technology, 4th Ed., Vol. 8, John Wiley & Sons, New York, 1996, page 334-348, such as sieve tray columns, bubble-cap tray columns, columns having structured packing or random packing, or single-stage evaporators such as falling-film evaporators, thin-film evaporators, flash evaporators, multiphase helical tube evaporators, natural circulation evaporators or forced circulation flash evaporators. The distillation may additionally be effected in one stage in the case of a partial evaporation of the feed stream.

In a preferred embodiment of the process according to the invention, column internals having structured packing are present in the distillation apparatus and generate preferably between 2 and 60, more preferably between 3 and 40, in particular between 4 and 20, separation stages.

In a particularly preferred embodiment of the process according to the invention, the at least one evaporator stage associated with the distillation apparatus of process step (2a) is designed in such a way that the material to be evaporated is subject to very little thermal damage, as achieved, for example, by falling-film evaporators, multiphase helical tube evaporators, thin-film evaporators or short-path evaporators, by short contact times of the material on the evaporator surface and very low temperatures of the evaporator surfaces.

In a preferred embodiment of the process according to the invention, the distillation apparatus of process step (2a) is operated with a divided column bottom as described in DE-A-102 004 004 724.

In a further preferred embodiment of the process according to the invention, the distillation may be performed with a direct condenser, so that the condensation is carried out in a column section which is preferably equipped with a structured column packing, a collecting cup below this packing, a liquid draw from the collecting cup, a pumped circulation system attached to the liquid draw and having a pump and heat exchanger, and also at least one apparatus for applying the liquid stream pumped by circulation to the packing above the collecting cup.

In a further preferred embodiment of the process according to the invention, the condensation is carried out at the top of the distillation apparatus in such a way that a substream from the top discharge is flushed back into the condenser.

In order to achieve a very high process yield based on 1,3-butadiene despite the only partial conversion in process step (1), it is preferred that the stream of 1,3-butadiene obtained as an azeotrope (stream 2) is recycled into process step (1). The recycling into process step (1) may, if appropriate, also only be partial.

The absolute pressure in process step (2a) is preferably from 0.001 to 100 bar, more preferably from 0.01 to 10 bar, in particular from 0.5 to 5 bar. The distillation is carried out in such a way that the temperature in the bottom of the distillation apparatus is preferably from 30 to 140° C., more preferably from 50 to 150° C., in particular from 60 to 120° C. The distillation is carried out in such a way that the condensation temperature at the top of the distillation apparatus is preferably from −50 to 150° C., more preferably from −15 to 60° C., in particular from 5 to 45° C. In a particularly preferred embodiment of the process according to the invention, the aforementioned temperature ranges are maintained both at the top and in the bottom of the distillation apparatus.

In process step (2a), an azeotrope of 1,3-butadiene and hydrogen cyanide is removed from the hydrocyanation stream. The remaining hydrocyanation stream may subsequently be transferred in a process step (2b) into a further distillation apparatus.

Process step (2b) of the process according to the invention may be carried out in any suitable apparatus known to those skilled in the art. Suitable apparatus for the distillation is as described, for example, in: Kirk-Othmer, Encyclopedia of Chemical Technology, 4th Ed., Vol. 8, John Wiley & Sons, New York, 1996, page 334-348, such as sieve tray columns, bubble-cap tray columns, columns having structured packing or random packing, or single-stage evaporators such as falling-film evaporators, thin-film evaporators, flash evaporators, multiphase helical tube evaporators, natural circulation evaporators or forced circulation flash evaporators. The distillation may be carried out in a plurality of, such as two or three, apparatuses, preferably in one apparatus.

In a particularly preferred embodiment, the distillation apparatus in process step (2b) is operated in stripping mode.

The distillation apparatus is preferably equipped with a structured packing which generates from 2 to 50, more preferably from 3 to 40, in particular from 4 to 30, theoretical plates.

In a particularly preferred embodiment of the process according to the invention, the at least one evaporator stages associated with the distillation apparatus of process step (2b) are designed in such a way that the material to be evaporated is subject to very little thermal damage, as achieved, for example, by falling-film evaporators, multiphase helical tube evaporators, thin-film evaporators or short-path evaporators, by short contact times of the material on the evaporator surface and very low temperatures of the evaporator surfaces.

The absolute pressure in process step (2b) is preferably from 0.001 to 10 bar, more preferably from 0.010 to 1 bar, in particular from 0.020 to 0.5 bar. The distillation is carried out in such a way that the temperature in the bottom of the distillation apparatus is preferably from 30 to 140° C., more preferably from 40 to 130° C., in particular from 50 to 120° C. The distillation is carried out in such a way that the condensation temperature at the top of the distillation apparatus is preferably from −20 to 140° C., more preferably from −10 to 80° C., in particular from −5 to 60° C. In a particularly preferred embodiment of the process according to the invention, the aforementioned temperature ranges are maintained both at the top and in the bottom of the distillation apparatus.

In order to increase the process yield of 1,3-butadiene used in the process according to the invention, it is preferred that the stream, obtained overhead in process step (2b), comprising 1,3-butadiene and any further hydrogen cyanide distilled off azeotropically with 1,3-butadiene is recycled into process step (1). The recycling into process step (1) may, if appropriate, also only be partial. Before it is recycled, the recycled stream may additionally be subjected to an operation for the purposes of the process, for example a compression to a higher pressure.

In a particularly preferred embodiment of the process according to the invention, the stream obtained overhead in process step (2b) is recycled via process step (2a) into process step (1).

In a further preferred embodiment of the process according to the invention, the distillation is carried out at average residence times of the liquid phase in the bottom region of the one or more distillation apparatuses of process step (2a) and (2b) of together less than 10 hours, more preferably less than 5 hours, in particular less than 1 hour.

The distillation is preferably carried out in such a way that the amount of 1,3-butadiene recycled to process step (1) contains from 1 to 1000 ppm by weight, more preferably from 2 to 500 ppm by weight, especially preferably from 5 to 200 ppm by weight, of 2-methyl-3-butenenitrile. This is achieved, for example, by suitable selection of the reflux ratio of the condensed 1,3-butadiene-containing top stream of step (2) on the suitable distillation apparatus.

The present invention further provides the use of 1,3-butadiene for azeotropically distilling hydrogen cyanide.

EXAMPLE

A reaction effluent 1a from the hydrocyanation of butadiene is fed from 16 bar reaction pressure via a flash vessel directly into a distillation column having stripping and rectifying sections. The column is equipped with a MontzPak type B1-350 packing. The rectifying section has an internal diameter of 200 mm and a height of 3 m, the stripping section an internal diameter of 80 mm and a height of 2.5 m. The column is operated with a forced-circulation evaporator with evaporator surface area 1.1 m$^2$, which is charged by a pump. The condensation is effected using a tube bundle heat exchanger with heat transfer surface area 2.2 m$^2$. The condenser is cooled with brine. The bottom evaporator is heated with steam.

The bottom of the distillation column is designed as a divided bottom. On the reflux side of the divided bottom, a stream 1b is fed in. On the evaporator side of the bottom, a thermoelement in a nozzle is used to measure a temperature of 90° C. The top pressure is 2.02 bar and the pressure drop is established over the column. The bottom draw stream 2s is likewise listed in table 1.

The condensate stream has an output temperature of 15° C. The output of the condenser flows through a pipeline having an internal diameter of 10 mm. On the exterior of this tube is mounted firstly a capacitive sensor from Endress and Hauser, Multicap DC 16. This signal sensor is calibrated to hydrogen cyanide concentrations in butadiene according to table 3. Flow through the line results in a measurement signal of 27.0% of the maximum analog output signal. The condensate is collected in a stainless steel vessel cooled to 0° C. and mixed there with fresh butadiene (stream 2b). From this vessel, the amount of reflux to the column head and the amount of butadiene drawn off to charge the hydrocyanation are drawn off in a ratio of 1 to 7. The composition of the draw stream 2a can likewise be read off in table 1.

Stream 1a contains 0.03% by weight hydrogen cyanide, stream 2s 0.41% by weight and stream 2a 0.03% by weight (determination by absorption of a defined sample in sodium hydroxide solution and subsequent argentometric cyanide titration). Stream 2b is commercial butadiene and is free of hydrogen cyanide. Further concentrations in the streams in table 1 were determined by GC analysis (Hewlett-Packard 5890 GC, HP 50-1 column, benzonitrile internal standard).

TABLE 1

Stream compositions

| | Stream 1a % by wt. | Stream 1b % by wt. | Stream 2s % by wt. | Stream 2a % by wt. | Stream 2b % by wt. |
|---|---|---|---|---|---|
| Hydrogen cyanide (titration) | 0.03 | 4.5 | 0.41 | 0.03 | 0.00 |
| 1,3-Butadiene | 9.1 | 31.7 | 2.9 | 99.8 | 90.0 |
| 3-Pentenenitrile | 33.1 | 0.5 | 35.0 | 0.0 | 0.0 |
| 2-Methyl-3-butenenitrile | 29.6 | 4.9 | 31.8 | 0.0 | 0.0 |
| 2-Methylglutaronitrile | 3.7 | 0.0 | 3.9 | 0.0 | 0.0 |
| 1-Butene | 2.7 | 7.3 | 0.7 | 0.0 | 5.5 |
| 2-Butene | 2.2 | 50.8 | 4.6 | 0.2 | 4.5 |
| Adiponitrile | 3.7 | 0.0 | 3.9 | 0.0 | 0.0 |

The remaining concentration up to 100% by weight in streams 1a and 2s results from the presence in the reaction effluent of catalyst components. These are Ni(0) complexes of the ligand of the formula A and free ligand of the formula A.

Formula A:

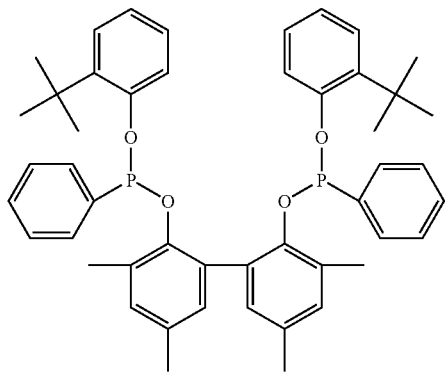

The mass flow rates measured are compiled in table 2.

TABLE 2

Stream flow rates

| Stream number | Mass flow rate |
|---|---|
| 1a | 60.4 kg/h |
| 1b | 5.0 kg/h |
| 2s | 57.1 kg/h |
| 2a | 29.6 kg/h |
| 2b | 21.2 kg/h |

TABLE 3

Calibration of capacitive probe at 15° C.

| Hydrogen cyanide content in 1,3-butadiene | Output signal relative to maximum output signal |
|---|---|
| 0.0% by wt. | 25.3% |
| 0.8% by wt. | 34.5% |

What is claimed is:

1. A process for reducing the content of hydrogen cyanide in mixtures comprising pentenenitriles and hydrogen cyanide, the process comprising azeotropically distilling the mixtures to remove the hydrogen cyanide with 1,3-butadiene.

2. The process according to claim 1,
    (1) providing a hydrocyanation stream which comprises 3-pentenenitrile, 2-methyl-3-butenenitrile, hydrogen cyanide, 1,3-butadiene and at least one hydrocyanation catalyst,
    (2) removing a mixture of hydrogen cyanide and 1,3-butadiene which forms an azeotrope from the hydrocyanation stream by distillation.

3. The process according to claim 2, wherein the 1,3-butadiene used in process step (2) stems from process step (1).

4. The process according to claim 2, wherein the 1,3-butadiene used in process step (2) is added to the hydrocyanation stream before the azeotropic distillation.

5. The process according to claim 2, wherein the 1,3-butadiene used in process step (2) partly stem from process step (1) and is partly added to the hydrocyanation stream before the azeotropic distillation.

6. The process according to claim 2, wherein all of the 1,3-butadiene which is added in process step (1) is added to the stream which is conducted from process step (1) to process step (2), and is recycled from process step (2) into process step (1).

7. The process according to claim 2, wherein the hydrocyanation catalyst used in process step (1) is a nickel (0) catalyst.

8. The process according to claim 2, wherein the pentenenitrile-containing mixture or the hydrocyanation stream obtained in process step (1) has at least one of the following contents:
    from 10 to 99% by weight of pentenenitriles comprising trans-3-pentenenitrile, 2-methyl-3-butenenitrile and also further pentenenitrile isomers, the ratio of 2-methyl-3-butenenitrile to trans-3-pentenenitrile being from 0.1:1 to 5:1
    from 0 to 60% by weight of 1,3-butadiene;
    from 0.01 to 30% by weight of catalyst components including catalyst dripping products; or
    from 0 to 10% by weight of hydrogen cyanide.

9. The process according to claim 1, wherein the azeotropic distillation of 1,3-butadiene and hydrogen cyanide is effected at a temperature in the bottom of a suitable distillation apparatus of from 30 to 250° C. and at a temperature in the condensation in a suitable distillation apparatus of from −50 to 150° C.

10. The use of 1,3-butadiene for azeotroppically distilling hydrogen cyanide.

11. The process according to claim 9, wherein the condensation is conducted at a pressure of from 0.001 to 100 bar.

* * * * *